(12) United States Patent
Callede

(10) Patent No.: US 9,125,637 B2
(45) Date of Patent: Sep. 8, 2015

(54) METHOD OF LOADING A LOCKED TISSUE BIOPSY NEEDLE INTO A BIOPSY GUN

(71) Applicant: Coloplast A/S, Humlebaek (DK)

(72) Inventor: David Callede, Sarlat la Canede (FR)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/615,513

(22) Filed: Feb. 6, 2015

(65) Prior Publication Data

US 2015/0150543 A1      Jun. 4, 2015

Related U.S. Application Data

(63) Continuation of application No. 13/389,804, filed as application No. PCT/DK2010/050208 on Aug. 12, 2010, now abandoned.

(30) Foreign Application Priority Data

Aug. 12, 2009   (EP) .................................... 09290626
May 6, 2010    (EP) .................................... 10290244

(51) Int. Cl.
    *A61B 10/02*       (2006.01)
(52) U.S. Cl.
    CPC ..... *A61B 10/0233* (2013.01); *A61B 2010/0208* (2013.01)

(58) Field of Classification Search
    CPC ............... A61B 10/02; A61B 10/0233; A61B 10/0266; A61B 2010/0208
    See application file for complete search history.

(56) References Cited

U.S. PATENT DOCUMENTS

| | | | | |
|---|---|---|---|---|
| 6,749,576 B2 * | 6/2004 | Bauer | ........................... | 600/567 |
| 7,588,546 B2 * | 9/2009 | de Andrade | .................... | 600/567 |
| 7,794,411 B2 * | 9/2010 | Ritchart et al. | ............... | 600/567 |
| 8,052,616 B2 * | 11/2011 | Andrisek et al. | .............. | 600/567 |
| 8,172,773 B2 * | 5/2012 | Heske et al. | ................... | 600/567 |
| 8,480,595 B2 * | 7/2013 | Speeg et al. | .................... | 600/568 |
| 2009/0112119 A1 * | 4/2009 | Kim | .............................. | 600/564 |

* cited by examiner

*Primary Examiner* — Max Hindenburg
(74) *Attorney, Agent, or Firm* — Coloplast Corp., Coloplast A/S; Nick Baumann

(57) ABSTRACT

A method of loading a locked tissue biopsy needle into a biopsy gun includes rotating a head of the biopsy gun in a first direction, with the head located at a front distal portion of the biopsy gun. The method includes inserting the locked tissue biopsy needle into a distal end of the head of the biopsy gun. The locked tissue biopsy needle provides a stylet inserted in a longitudinal lumen of a cannula, and the stylet is locked in position relative to the cannula thus preventing longitudinal movement of the stylet within the cannula. The method includes rotating the head of the biopsy gun in a second direction opposite from the first direction and rotating the stylet relative to the cannula and unlocking the stylet from the cannula allowing longitudinal movement of the stylet within the cannula.

10 Claims, 9 Drawing Sheets

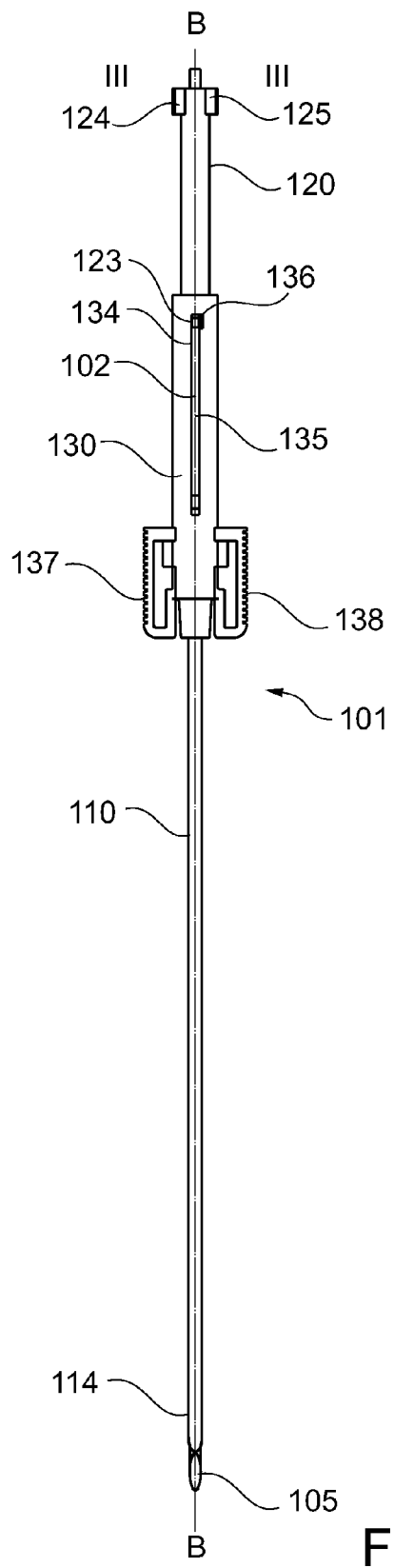
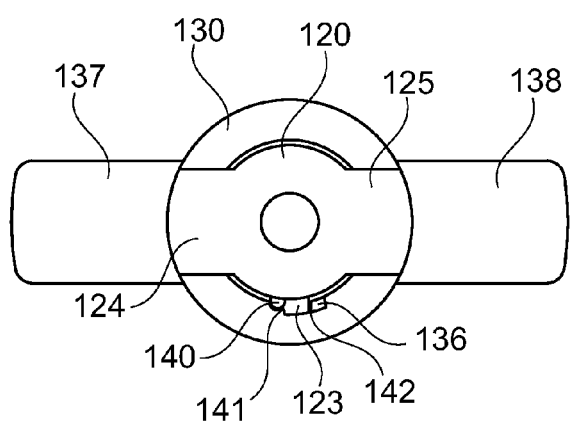
Fig. 3
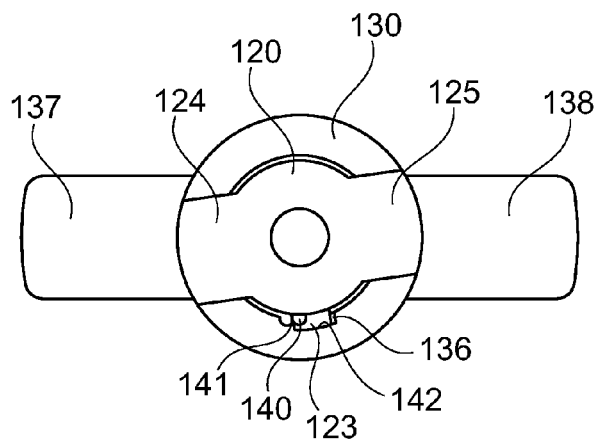
Fig. 4
Fig. 2

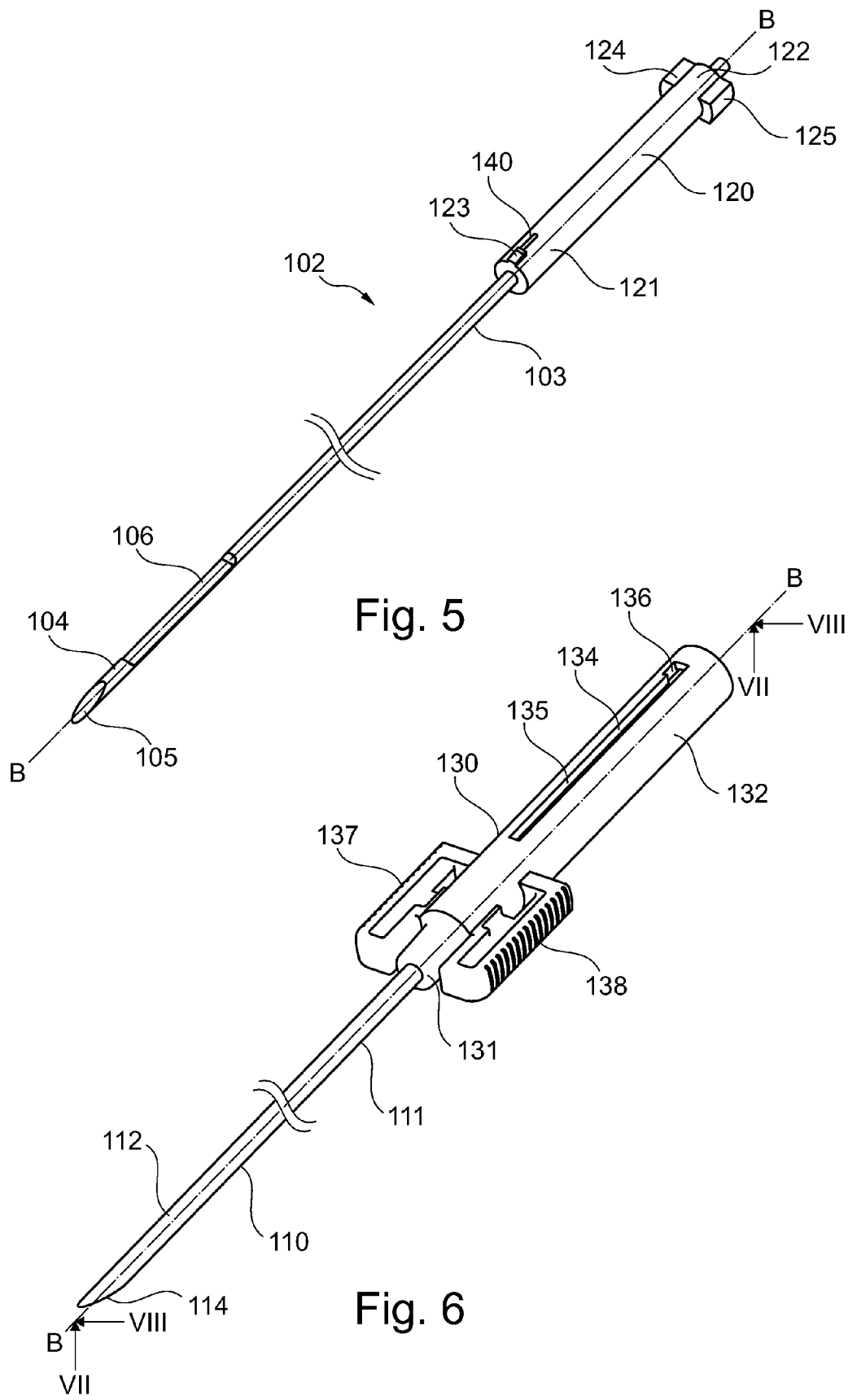

METHOD OF LOADING A LOCKED TISSUE BIOPSY NEEDLE INTO A BIOPSY GUN

TECHNICAL FIELD

The invention relates to a biopsy needle wherein the cannula and stylet may be arranged in a locked position, preventing longitudinal movement relative to each other, and a reusable biopsy gun comprising means for moving the biopsy needle from its locked position to an unlocked position where the cannula and stylet may be moved in the longitudinal direction relative to each other. The invention furthermore relates to a kit comprising at least one biopsy needle and a biopsy gun as described herein.

BACKGROUND

The use of a reusable biopsy gun and a biopsy needle comprises a number of steps.

In a first step, the biopsy needle is loaded into the biopsy gun.

In a second step the biopsy gun is armed, this is typically done by compressing two springs, one for the cannula of the biopsy needle and one for the stylet of the biopsy needle.

In a third step the biopsy needle is inserted into the sampling site, e.g. soft tissue for example from the prostate, from which samples are desired.

Finally, in a fourth step, the biopsy gun is fired, e.g. when the gun has been armed by springs these are released. This will result in the stylet being fired first. The stylet is provided with a small recess at the tip into which sample tissue will move. Secondly, the cannula is fired which cuts off the sample tissue and contains it in the recess. The biopsy needle is then pulled out of the body and the sample tissue may be retrieved.

The steps may vary a little, and other steps may be introduced in between, however, most procedures generally follow the above.

The present invention relates primarily to the first step. Loading of the biopsy needle into the biopsy gun comprises a number of handling issues. In particular because the nurse or surgeon has to handle two separate elements, one of which is very sharp and thus may involve unintentionally puncturing of the protective barrier, such as gloves, and even the tissue of the person loading the needle into the gun.

In a number of known biopsy needles, the cannula and stylet are freely slidable relative to each other when loading the biopsy needle into the biopsy gun. This results in a high risk of the person handling the gun being pierced when loading the gun.

In order to overcome this, some biopsy needles have been formed with locking members in order to prevent unintentional sliding movement between the cannula and the stylet. However, these comprise a third element which has to be removed before or after loading of the needle. Furthermore, during manufacture such a third element adds to the cost of the biopsy needle.

Moreover, using such needles with known biopsy guns poses another problem in that the known biopsy guns are not adapted to handle such an additional element. Thus, the locking element has to be removed prior to loading, thereby removing the advantage of having a locked relationship between cannula and stylet during this step.

Thus, there is both a need for providing a biopsy needle that solves the issues addressed above and a biopsy gun suitable for use with such a biopsy needle.

BRIEF DESCRIPTION

An aspect of the invention is to provide a biopsy needle comprising a stylet extending along an axis A-A between a proximal stylet end and a distal stylet end, the biopsy needle further comprising a cannula extending along the axis A-A between a proximal cannula end and a distal cannula end at least partly enclosing the stylet, wherein the stylet and the cannula are rotatable relative to each other around the axis A-A between a locked position wherein relative movement between the stylet and the cannula along the axis A-A is prevented, and an unlocked position wherein relative movement between the stylet and the cannula along the axis A-A is enabled.

This facilitates the loading of the biopsy needle into a biopsy gun as a biopsy needle is provided which is interchangeable between two positions, a locked position which is suitable when the biopsy needle is loaded into the biopsy gun without the operator having to be worried whether the stylet and the cannula will move relative to each other and an unlocked position wherein the biopsy needle is ready for use, i.e. the cannula and the stylet are movable relative to each other in the longitudinal direction.

In one embodiment the biopsy needle is a biopsy needle for use in a biopsy gun. The biopsy needle will typically be adapted for replaceable arrangement in the biopsy gun and in such configuration the biopsy needle will typically be a single use biopsy needle. However, in some cases the biopsy needle could be separately sterilized or otherwise cleaned in order for multiple uses.

In one embodiment of the biopsy needle as described above, a stylet coupling part is arranged at the proximal end of the stylet, and a cannula coupling part is arranged at the proximal end of the cannula. The coupling parts are typically moulded onto the respective proximal ends, for example by injection moulding. The parts can be formed in many sizes and shapes suitable for the specific needs.

This further facilitates the handling of the biopsy needle as the operator is able to manipulate the respective coupling parts instead of the sharp and often relatively thin stylet and cannula parts of the biopsy gun.

Throughout the specification when using the word 'proximal' referral is made to an end of a part or element that is closest to user when the needle is inserted into the patient. The opposite end of the same part or element is referred to as the 'distal' end.

In one embodiment, the rotatable movement of the stylet and the cannula relative to each other between the locked and the unlocked position can be provided by forming the cannula coupling part with a tubular coupling member having a tubular compartment for at least partly receiving the stylet coupling part, wherein the tubular compartment is formed with a track which engages with a protrusion formed on the stylet coupling part.

The track thus functions as a limit for the protrusion, thereby controlling the relative movement between the cannula and the stylet. Thus, by defining the shape of the track, it is possible to limit the pattern and/or extent of movement between the cannula and the stylet.

In one embodiment, the track is made up of at least a first and a second leg, the first leg extending circumferentially around the axis A-A, and the second leg extending longitudinally along the axis A-A.

It can be understood that when the protrusion travels in the first leg which extends mainly transversely to the longitudinal axis A-A, movement of the cannula and the stylet relative to each other along the axis A-A is limited, however, when the protrusion moves into the second leg, the cannula and the stylet are freely movable relative to each other along the axis A-A within the extent of the second leg.

In one embodiment, the biopsy needle is provided with a coupling arrangement which allows the protrusion to be moved between the first leg and the second leg via plastic deformation of at least one of the stylet coupling part or the cannula coupling part. This provides an added level of security, as additional force must be applied in order to move the biopsy needle between its locked and unlocked position.

In another embodiment, at least one rib is arranged on an outer surface of either the cannula coupling part or the stylet coupling part, and at least one tab is arranged on an outer surface of the other coupling part.

The rib and tab facilitate the rotational movement between the locked and unlocked position, as these function as gripping means. For example, an operator can easily manipulate the rib and tab relative to each other.

Alternatively, a biopsy gun can comprise activation means for at least moving the biopsy needle from the locked position to the unlocked position. Such activation means can for example be provided by a protrusion in the housing of the biopsy gun, e.g. in the lid, which engages with either the rib or the tab when the biopsy gun is closed and thereby rotates the cannula and the stylet relative to each other by engagement of the rib or the tab with the protrusion.

The biopsy needle may be provided in a kit comprising a number of biopsy needles as described above and a biopsy gun for use with said biopsy needle. Of course, the parts may also be provided separately.

In one aspect, the invention relates to a biopsy gun. In particular, it relates to a biopsy gun where the biopsy needle may be front loaded.

In such an aspect, the invention relates to a biopsy gun for loading, arming and firing a biopsy needle for receiving a biopsy sample, wherein the biopsy gun comprises a cannula slide adapted for engaging with a cannula of a biopsy needle and a stylet slide adapted for engaging with a stylet of a biopsy needle, the cannula slide and the stylet slide being slidable relative to each other along an axis C-C between a proximal end through which a biopsy needle extends out through the biopsy gun when a biopsy needle is inserted and a distal end, and where the cannula slide comprises cannula coupling means adapted for coupling with a cannula of a biopsy needle when the cannula slide and cannula are rotated relative to each other around axis C-C, and where the stylet slide comprises stylet coupling means adapted for coupling with a stylet of a biopsy needle when the stylet slide and stylet are rotated relative to each other around axis C-C.

By using rotational coupling between the cannula and stylet of the biopsy needle and the respective slide, it is possible to provide front loading of the biopsy needle into the biopsy gun, i.e. the biopsy needle is introduced into the biopsy gun along the axis C-C, through the proximal end of the biopsy gun and then subsequently rotated into position. This provides an easy and intuitive loading of the biopsy gun.

In one embodiment, in order to provide relative movement between the cannula and the stylet and their respective slides, the biopsy gun further comprises activation means for rotating a biopsy needle around the axis C-C.

In another embodiment of the biopsy gun, the stylet slide is in the form of a stylet tube extending along axis C-C, and the cannula slide is in the form of a cannular tube extending along axis C-C, the stylet tube being at least partly slidably arranged inside the cannula tube. This provides a compact design wherein the displacement of the respective slides is controlled.

A number of different embodiments of the stylet and cannula coupling means may be provided. One such embodiment may be a bayonet type coupling which is safe and reliable. In such embodiment of the biopsy gun the proximal end of the stylet tube is formed with stylet coupling means in the form of at least one L-shaped stylet groove having a first leg extending longitudinal along axis C-C and a second leg extending transversely to the axis C-C, and wherein the proximal end of the cannula tube is formed with cannula coupling means in the form of at least one L-shaped cannula groove having a first leg extending longitudinal along axis C-C, and a second leg extending transversely to the axis C-C.

In one embodiment, the activation means may be in the form of a rotatable head arranged at the proximal end of the biopsy, i.e. at the end where the biopsy needle is loaded into the biopsy gun. This provides simple operation of the biopsy gun, as the head may easily be rotated after the biopsy needle has been loaded and thereby preparing the biopsy gun for arming.

In one embodiment, the rotatable head may function as a cover. This is advantageous since any blood or other liquid that runs from the introduction site and down along the biopsy needle will be caught by the head and this may be easily cleaned. In such embodiment, the rotatable head comprises a first through-going channel extending along axis C-C for receiving the biopsy needle.

Different countries have different requirements for sterilizing and cleaning reusable medical equipment such as the biopsy gun as described herein. Some places it is only necessary to sterilize the point of first contact with body fluids. In such cases, it is advantageous that the rotatable head is detachably arranged on the biopsy gun. Thus, the rotatable head may be removed and sterilized separately, typically in an autoclave, thereby avoiding that the entire biopsy gun has to be sterilized.

In another aspect, the invention relates to a kit comprising a biopsy gun as described above and at least one biopsy needle as described above for use with the biopsy gun.

BRIEF DESCRIPTION OF THE DRAWINGS

FIG. 2 shows another embodiment of a biopsy needle as described herein,

FIG. 3 shows a top view of the biopsy needle of FIG. 2 along lines III-III,

FIG. 4 shows an alternative position of the parts of the biopsy needle shown in the same view as FIG. 3, FIG. 5 shows, in perspective, a stylet of the biopsy needle of FIG. 2-4, FIG. 6 shows, in perspective, a cannula of the biopsy needle of FIG. 2-4.

DETAILED DESCRIPTION

Figure 1:
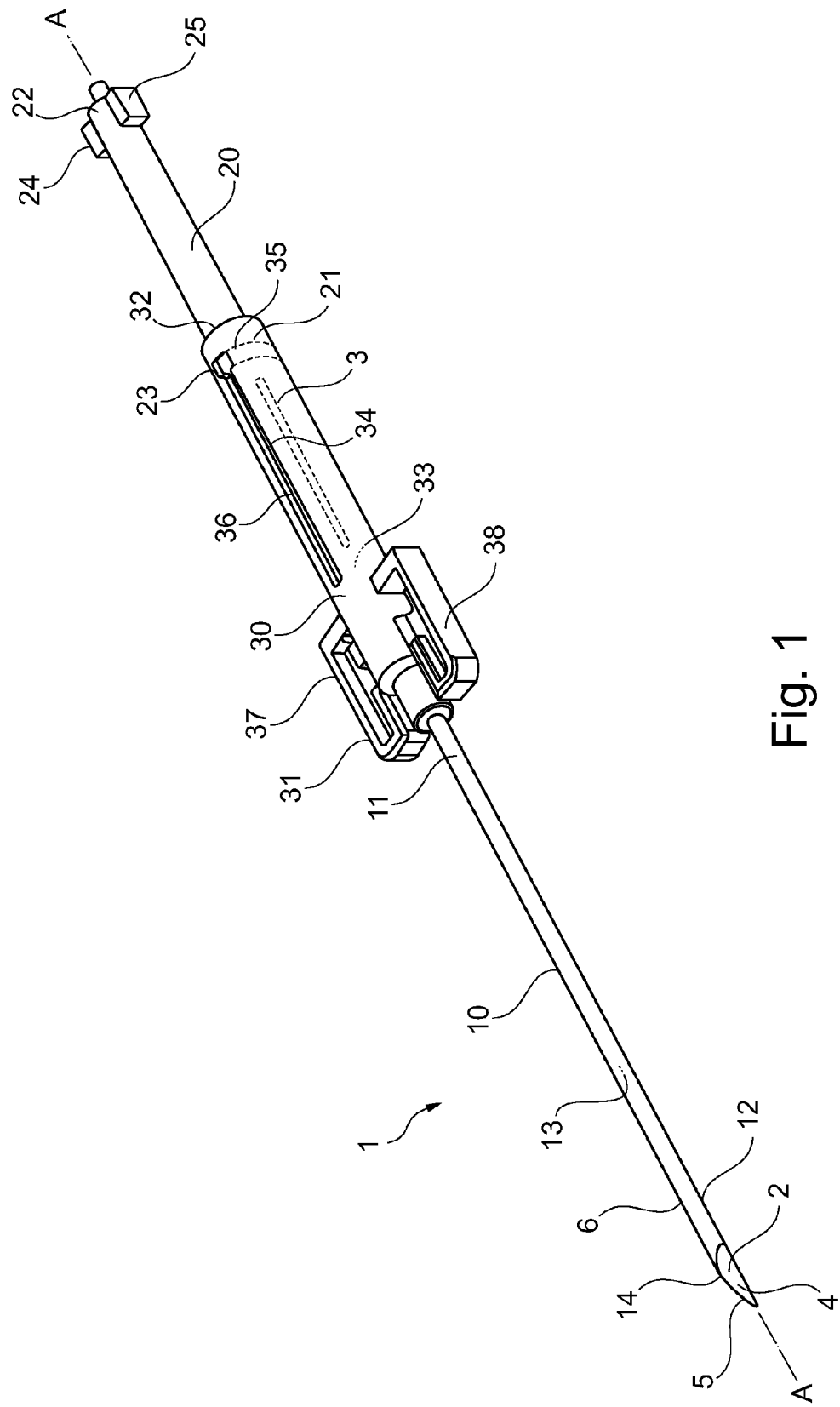
FIG. 1 shows one embodiment of a biopsy needle as described herein.
Figure 7:
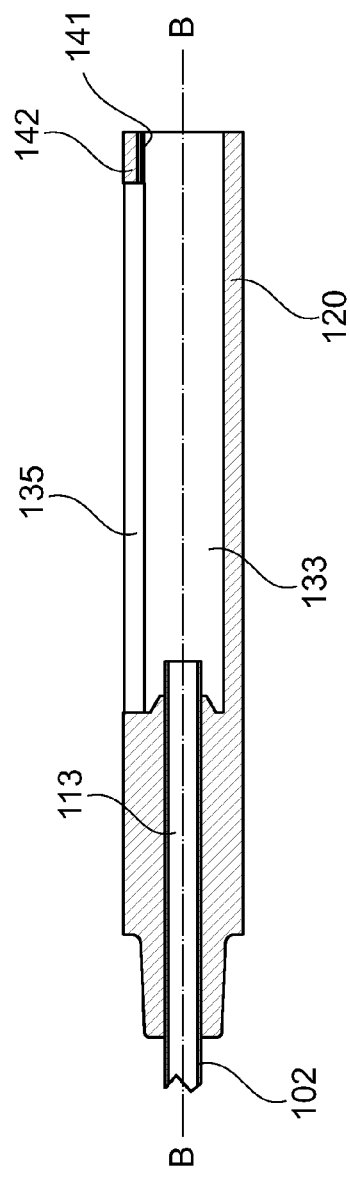
FIG. 7 shows the cannula of FIG. 6 in section along line VII-VII.
Figure 8:
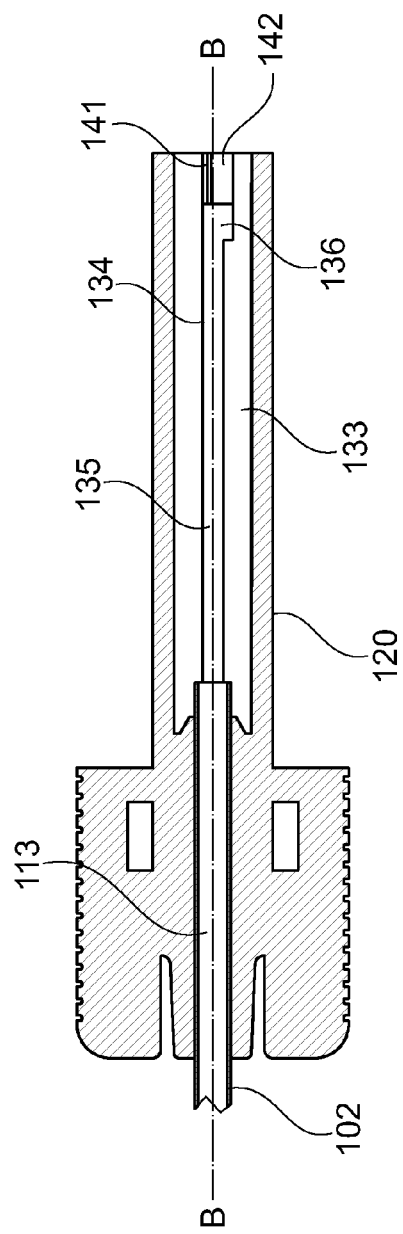
FIG. 8 shows the cannula of FIG. 7 in section along line VIII-VIII.

One embodiment of a biopsy needle 1 extending along a longitudinal axis A-A is shown in FIG. 1.

In the following, it should be understood that when referring to inner and outer surfaces of respective parts this is to be interpreted relative to the surface's orientation relative to the longitudinal axis A-A. Thus, an outer surface will face away from the longitudinal axis, while an inner surface will face towards the longitudinal axis.

The biopsy needle 1 comprises a stylet 2 extending longitudinally between a proximal stylet end 3 and a distal stylet end 4.

The stylet 2 terminates at the distal stylet end 4 in a stylet tip 5, which is sufficiently sharp to penetrate tissue. Further arranged at the distal stylet end 4 is a tissue recess 6 for receiving tissue samples during use of the biopsy needle.

The biopsy needle 1 further comprises a cannula 10 which extends longitudinally between a proximal cannula end 11 and a distal cannula end 12. The cannula 10 is provided with a first through-going tubular compartment 13 wherein at least a part of the stylet 2 may be received, or in other words the cannula 10 at least partly encloses the stylet 2, allowing the stylet to slide longitudinally along the axis A-A within the cannula 10.

The cannula 10 terminates at distal cannula end 12 in a cannula tip 14, which is sufficiently sharp to penetrate tissue.

A stylet coupling part 20 is attached to the proximal stylet end 3 at a distal stylet coupling part end 21. The stylet coupling part 20 is cylindrically formed and extends longitudinally between the distal stylet coupling part end 21 and a proximal stylet coupling part end 22.

A cannula coupling part 30 is attached to the proximal cannula end 11 at a distal cannula coupling part end 31. The cannula coupling part 30 extends longitudinally between the distal cannula coupling part end 31 and a proximal cannular coupling part end 32 and has a tubular cylindrical shape, defining a second through-going tubular compartment 33 which is in communication with the first through-going tubular compartment 13 and is capable of at least partly receiving the stylet 2 and the stylet coupling part 20.

A track 34, e.g. in the shape of a groove or a through-going slot, is formed on the inner surface of the cannula coupling part 30, i.e. the track 34 opens out into the second through-going tubular compartment 33. The track 34 is formed of a first and a second track leg 35, 36. The first track leg 35 extends annularly around the longitudinal axis A-A in the form a half-circle transversely to the longitudinal axis. The second track leg 36 extends from one end of the first track leg 35 in a direction along the longitudinal axis A-A. Thus, it can be understood that the track is L-shaped, where one of the legs of the L will curve and where the angle between the two legs are approximately 90°. However, other angles between the first and the second track leg can be provided, in particular angles between approximately 45° and 135°.

A coupling protrusion 23 is provided on the outer surface of the stylet coupling part 20, at its distal end 21. The coupling protrusion 23 has a dimension which allows it to be received in the track 34. Thus, when the stylet coupling part 20 is arranged in the second through-going tubular compartment 33 of the cannula coupling part 30 so that the coupling protrusion 23 extends into the track 34, the movement of the stylet 2 and the cannula 6 will be limited to the shape of the track 34.

In the current embodiment, the shape of the track 34 will thus limit relative movement between the stylet 2 and the cannula 6 along the longitudinal axis A-A, while the coupling protrusion 23 runs in the first track leg 35, which extends transverse to the longitudinal direction. In other words, the biopsy needle can be considered to be in a locked position wherein relative movement between the stylet and the cannula along the axis A-A is prevented.

However, by rotating the stylet 2 and the cannula 6 relative to each other around the axis A-A, the coupling protrusion 23 can be moved into the second track leg 36, which extends along the longitudinal direction. Thus, the biopsy needle can be considered to be in an unlocked position wherein relative movement between the stylet 2 and the cannula 6 along the axis A-A is enabled.

The biopsy needle as described above will typically be used in a biopsy gun (not shown) suitable for reuse, while the biopsy needle will be discarded after use.

Typical biopsy guns are formed with two slides on which the stylet coupling part 20 and the cannula coupling part 30 are placed, respectively. As is commonly known, such slides are individually moveable in order to move the stylet 2 and the cannula 10 relative each other.

Protruding from opposite sides of the outer surface of the cannula coupling part 30, a first and a second rib 37, 38 are arranged. When these ribs are arranged on the corresponding slide of the biopsy gun, the cannula coupling part 30, and thereby the cannula 6, is prevented from unintentionally rotating around the longitudinal axis.

Protruding from opposite sides of the outer surface of the stylet coupling part 20, a first and a second tab 24, 25 are arranged.

When the biopsy needle 1 has been arranged in the biopsy gun, i.e. the stylet coupling part 20 and the cannula coupling part 30 have been placed on the respective slides, the stylet coupling part 20 may be rotated around the longitudinally axis, moving the biopsy needle from its locked position to its unlocked position.

The first and the second tab 24, 25 facilitate this rotation, as these provide a gripping area on the stylet coupling part 20.

Thus, it can be understood that the biopsy needle can easily be arranged in the biopsy gun, without having to keep track of the relative placement of the stylet coupling part and the cannula coupling part, as these are locked. When arranged in the biopsy gun, the coupling parts are unlocked relative to each other and the biopsy needle is thus ready to use.

A second embodiment of the biopsy needle 101 extending along a longitudinal axis B-B is shown in FIGS. 2-6.

As with the first embodiment described above, it should be understood that when referring to inner and outer surfaces of respective parts this is to be interpreted relative to the surface's orientation relative to the longitudinal axis B-B. Thus, an outer surface will face away from the longitudinal axis, while an inner surface will face towards the longitudinal axis.

The biopsy needle 101 comprises a stylet 102 extending longitudinally between a proximal stylet end 103 and a distal stylet end 104.

The stylet 102 terminates at the distal stylet end 104 in a stylet tip 105, which is sufficiently sharp to penetrate tissue. Further arranged at the distal stylet end 104 is a tissue recess 106 for receiving tissue samples during use of the biopsy needle.

The biopsy needle 101 further comprises a cannula 110, which extends longitudinally between a proximal cannula end 111 and a distal cannula end 112. The cannula 110 is provided with a first through-going tubular compartment 113 wherein at least a part of the stylet 102 may be received, or in other words, the cannula 110 at least partly encloses the stylet 102, allowing the stylet to slide longitudinally along the axis B-B within the cannula 110.

The cannula 110 terminates at the distal cannula end 112 in a cannula tip 114, which is sufficiently sharp to penetrate tissue.

A stylet coupling part 120 is attached to the proximal stylet end 103 at a distal stylet coupling part end 121. The stylet coupling part 120 is cylindrically formed and extends longitudinally between the distal stylet coupling part end 121 and a proximal stylet coupling part end 122.

A cannula coupling part 130 is attached to the proximal cannula end 111 at a distal cannula coupling part end 131. The cannula coupling part 130 extends longitudinally between the distal cannula coupling part end 131 and a proximal cannular coupling part end 132 and has a tubular cylindrical shape, defining a second through-going tubular compartment 133 which is in communication with the first through-going tubular compartment 113 and is capable of at least partly receiving the stylet 102 and the stylet coupling part 120.

A track 134, e.g. in the shape of a groove or a through-going slot, is formed on the inner surface of the cannula coupling part 130 so that the track 134 opens out into the second through-going tubular compartment 133. The track 134 is formed of a longitudinal track leg 135 and a track recess 136 formed at the distal end of the longitudinal track leg and extending annularly around the longitudinal axis, or in other words the track recess 136 extends transverse from the longitudinal track leg 135. Similar to the first embodiment described above, the track 134 can be viewed as being L-shaped, where the track recess 136 will slightly curve and where the angle between the two legs is approximately 90°. However, other angles between the first and the second track leg can be provided, in particular angles between approximately 45° and 135°.

A coupling protrusion 123 is provided on the outer surface of the stylet coupling part 120, at its distal end 121. The coupling protrusion 123 has a dimension which allows it to be received in the track 134. Thus, when the stylet coupling part 120 is arranged in second through-going tubular compartment 133 of the cannula coupling part 130 so that the coupling protrusion 123 extends into the track 134, the movement of the stylet 102 and the cannula 106 will be limited to the shape of the track 134.

Extending longitudinally and in a proximal direction from the coupling protrusion 123, a first locking rib 140 is provided on the outer surface of the stylet coupling part 120. Extending longitudinal and in a proximal direction from the longitudinal track leg 135, a surface recess 142 is provided on the inner surface of the cannula coupling part. Said surface recess has a depth which allows the first locking rib 140 to move freely therein, when the stylet coupling part 120 is arranged in the cannula coupling part 130. A second locking rib 141 is provided in the surface recess on the inner surface of the cannula coupling part 130.

When the stylet coupling part 120 is arranged in the cannula coupling part 130, the first and the second locking rib are so dimensioned that they will abut against each other. However, by applying some force, plastic deformation may occur and the two locking ribs can pass each other, making it possible to arrange the stylet coupling part and the cannula coupling part in two distinct positions. In itself, this principle is generally known and is, for example, used in coupling arrangements such as in lids for markers and pens and a large number of other applications where at least one part is plastically deformed in order to fit or pass another part. A person skilled in the art would know how to dimension the first and the second locking ring depending on the material used in order to achieve the desired force required for the two locking ribs to pass each other.

In the second embodiment, a locked position can thus be provided wherein relative movement between the stylet and the cannula along the axis B-B is prevented as the coupling protrusion 123 is retained in the track recess 136 by first and second locking ribs. Then, by applying a predetermined amount of torque force, i.e. rotating the stylet coupling part 120 and the cannula coupling part 130 with respect to each other, the two locking ribs pass each other and the coupling protrusion is moved out of the track recess 136 and into the longitudinal track leg, thereby placing the biopsy needle in an unlocked position wherein relative movement between the stylet and the cannula along the axis B-B is enabled.

In FIG. 3, which is a top view along line III-III in FIG. 2, it is shown how the first locking rib 140 and the second locking rib 141 are positioned relative to each other when the biopsy needle is in its unlocked position, i.e. the coupling protrusion 123 is arranged in the longitudinal track leg 135.

In FIG. 4, a top view of the biopsy needle, corresponding to that of FIG. 3, is shown where the biopsy needle is in its locked position. Here, it can be seen that the first and second locking ribs are arranged opposite their relative position in the unlocked position whereby the coupling protrusion 123 is at least partly arranged in the track recess 136.

The biopsy needle as described above will typically be used in a biopsy gun (not shown) suitable for reuse while the biopsy needle will be discarded after use.

As described above with respect to the first embodiment, typical biopsy guns are formed with two slides on which the stylet coupling part 120 and the cannula coupling part 130 are placed, respectively. As is commonly known, such slides are individually moveable in order to move the stylet 102 and the cannula 110 relative each other.

Protruding from opposite sides of the outer surface of the cannula coupling part 130, a first and a second rib 137, 138 are arranged. When these ribs are arranged on the corresponding slide of the biopsy gun, the cannula coupling part 130, and thereby the cannula 106, is prevented from unintentionally rotating around the longitudinal axis.

Protruding from opposite sides of the outer surface of the stylet coupling part 120, a first and a second tab 124, 125 are arranged.

When the biopsy needle 101 has been arranged in the biopsy gun, i.e. the stylet coupling part 120 and the cannula coupling part 130 have been placed on the respective slides, the stylet coupling part 120 may be rotated around the longitudinally axis, moving the biopsy needle from its locked position to its unlocked position.

The first and the second tab 124, 125 facilitate this rotation as these provide a gripping area on the stylet coupling part 120.

Thus, it can be understood that the biopsy needle can easily be arranged in the biopsy gun without having to keep track of the relative placement of the stylet coupling part and the cannula coupling part, as these are locked. When arranged in the biopsy gun, the coupling parts are unlocked relative to each other and the biopsy needle is thus ready to use.

FIGS. 9-15 shows a biopsy gun 200 which is particularly suited for use with the biopsy needle 101 as described above with reference to FIGS. 2-8.

Figure 9:
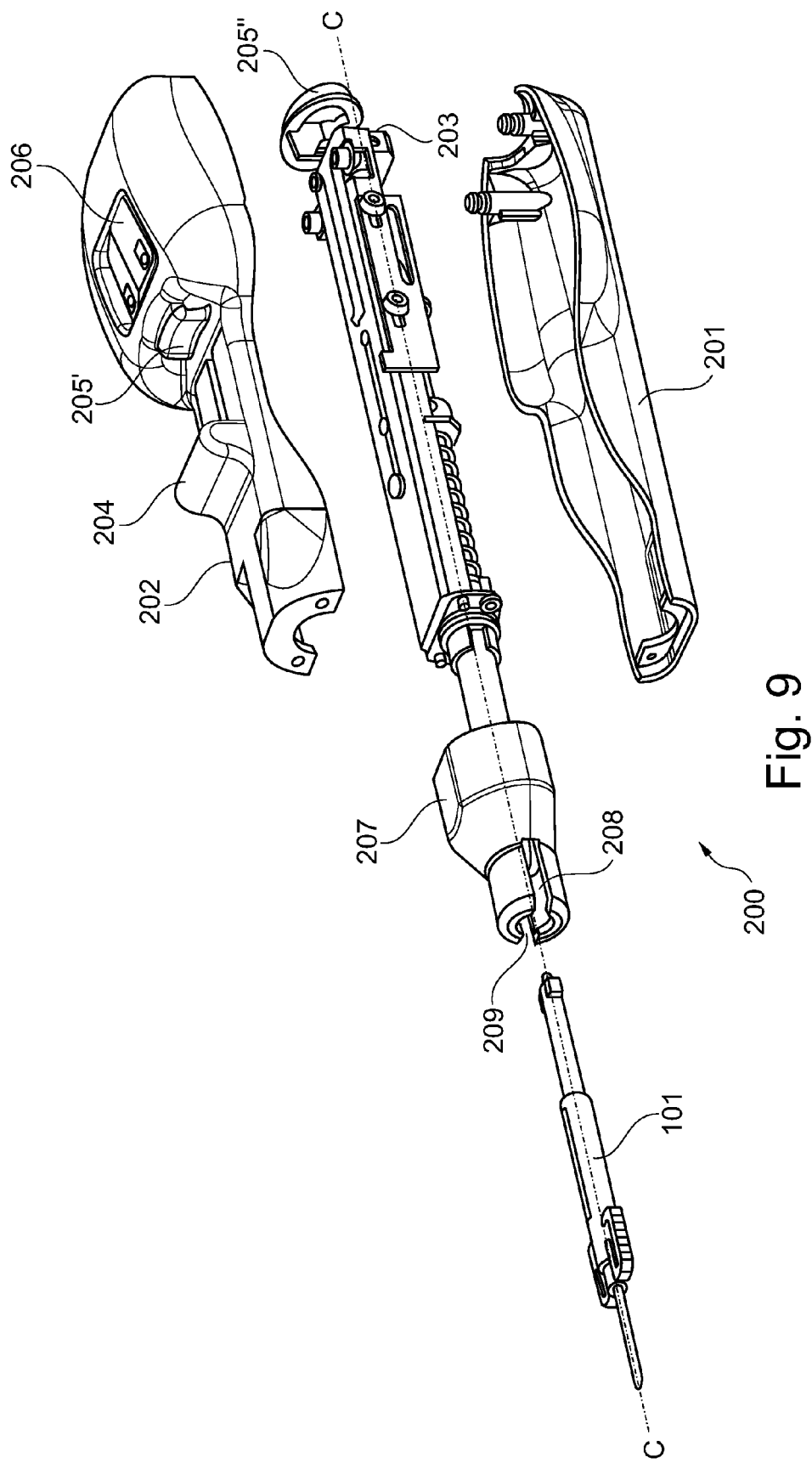
FIG. 9 shows, in exploded view, an embodiment of a biopsy gun to be used with the biopsy needles as described herein.

In FIG. 9, the biopsy gun 200 is shown in exploded view. The biopsy gun comprises a housing in the form of an upper part 201 and a lower part 202. Within the housing 201, 202, the gun mechanics 203 are contained.

The housing can be removed partially or completely in order to have access to the mechanical system 203, for example in order to clean it or change parts.

The gun has an arming slider 204 which is used for arming the biopsy needle and two release buttons 205', 205".

A safety switch 206 is provided which is movable between a safe position wherein firing of the biopsy gun is not possible and a release position wherein firing of the biopsy gun is allowed.

A rotatable head 207 is arranged at the proximal end of the biopsy gun. The rotatable head is rotatable around axis C-C of the biopsy gun. A first and second recess 208, 209 are provided in the rotatable head 207 for receiving the first and second rib 137, 138 of the biopsy needle 101. Thus, when the head is rotated the biopsy needle is rotated along with it.

FIGS. 10-13 shows, in section, the biopsy gun and biopsy needle seen from above, i.e. looking down on the upper part 201 of the housing.

Figure 11:
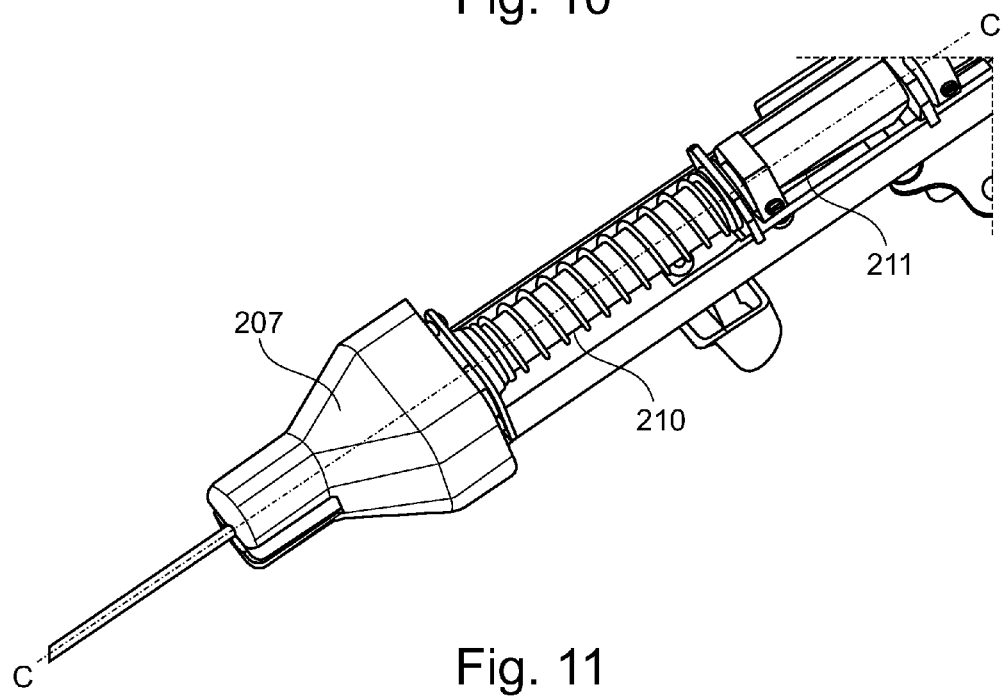
Figure 12:
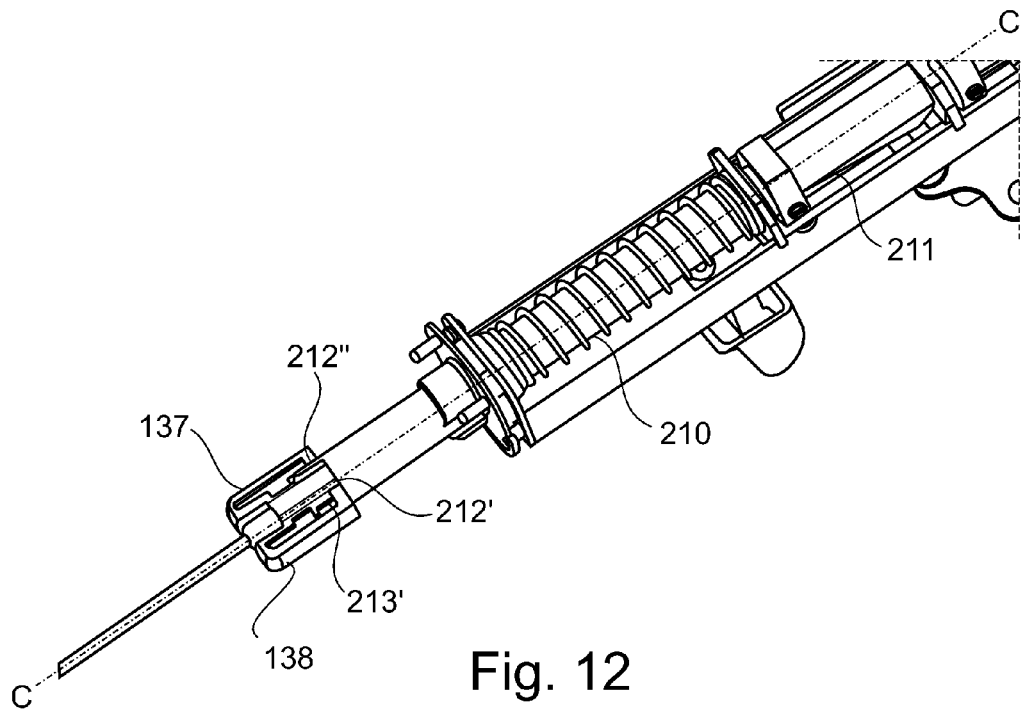
Figure 13:
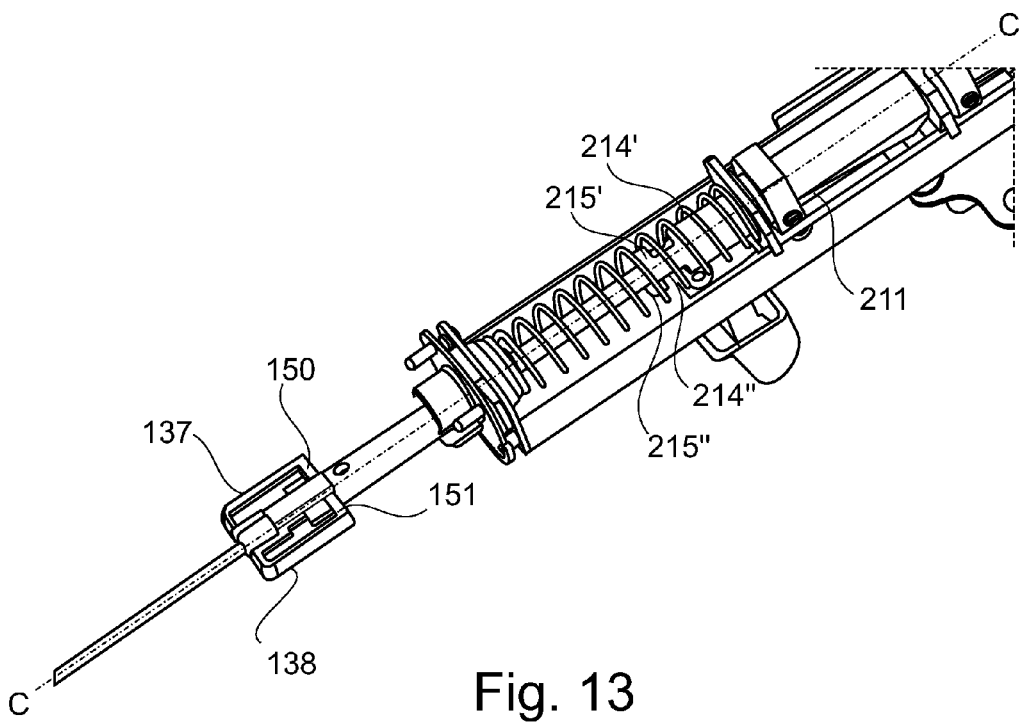

In order to facilitate viewing, FIGS. 11-13 are shown with some parts hidden. In FIGS. 11-13 the housing 201, 202 are hidden, thus exposing the gun mechanics. In FIG. 12, the rotatable head 207 is hidden and FIG. 13 further hides the cannula tube 210.

A cannula slide in the form of a cannula tube 210 and a stylet slide in the form of a stylet tube 211 are provided in the gun mechanics.

A first and second cannula groove 212', 212" are provided in the proximal end of the cannula tube 210. The cannula grooves are L-shaped resulting in a first and a second cannula coupling tab 213', 213".

A first and a second stylet groove 214', 214" are provided in the proximal end of the stylet tube 211. The stylet grooves are L-shaped resulting in a first and a second stylet coupling tab 215', 215".

It should be understood that the L-shaped grooves are so dimensioned that a first leg extends parallel to the longitudinal axis C-C from the proximal edge of the respective tubes, and then continues into a second leg that extends transversely to the longitudinal axis C-C, thereby providing an L-shape.

When loading the biopsy needle, the rotatable head is rotated approximately 90° around axis C-C which allows the biopsy needle to be inserted into the biopsy gun in such a way that the first and the second stylet tab 124,125 of the biopsy needle are received within the first legs of the stylet grooves, the first and the second cannula tab 150,151 are received within the first legs of the cannula grooves and the first and the second rib are received in the first and second recess 208,209 of the rotatable head.

Thus, when the head is rotated approximately 90° into the position as shown in FIGS. 10-13, the first and the second recesses will engage with the first and the second rib, thereby turning the biopsy needle around the axis C-C, corresponding to the axis B-B of the biopsy needle. This results in the first and the second stylet tab 124,125 being moved into the second leg of the stylet grooves, and the first and the second cannula tabs 150,151 are moved into the second leg of the cannula groove. This bayonet coupling between the respective tabs and grooves couples the cannula with the cannula slide and the stylet with the stylet slide.

Furthermore, by providing a difference in the length of the second leg of the cannula grooves compared to the stylet groove, it is possible to move the biopsy needle from its locked position to its unlocked position in the same rotation as it takes to couple the cannula and stylet with their respective slides. This provides an intuitive and all-in-one step for the surgeon, thereby facilitating the use of the biopsy gun. In the present embodiment, this is achieved by having the second legs of the cannula grooves so much longer that the first and second stylet tabs will reach the bottom of the second leg of the stylet grooves before the first and second cannula tabs reach the bottom of the second leg of the cannula grooves.

With the biopsy needle loaded into the biopsy gun and in the unlocked position, it is now possible for the surgeon to arm the biopsy gun, insert it into the sample site and fire it in order to retrieve a sample.

Arming of the biopsy gun is typically performed as a two-step process. In the first step the arming slider 204 is pulled back along axis C-C. Engagement means (not shown) couples the arming slider with the cannula slider, e.g. the cannula tube 210, resulting in the fact that the cannula slider is pulled back together with the arming slider. As the cannula slider is pulled back the cannula firing means are tensioned. Such firing means are typically in the form of a cannula spring 300. When pulled back to a desired position the cannula slider and the cannula spring are locked in this position. This position is also referred to as the armed position of the cannula slider.

After arming the cannula slider, the arming slider uncouples from the cannula slider. Such uncoupling can be realised in different ways, many of which are already teached within the art. One way is to provide a track (not shown), which guides the arming slider and thus guides the arming slider away from the cannula slider after the cannula slider has been armed.

The arming slider is then pushed forward. This can be done by the surgeon, or a spring may pull the arming slider forward where it engages the stylet slider. The stylet slider is then moved into its armed position in the same manner as the cannula slider.

With both the cannula slider and the stylet slider in their respective armed positions, the biopsy gun is now considered armed.

The surgeon may now insert the needle into the sample site and fire the biopsy gun in order to retrieve a sample.

When inserted, the surgeon pushes one of the release buttons 205', 205". When pressed, the release button unlocks the stylet slider from its arming position. The force released by the stylet firing means, such as a spring, fires the stylet slider forward. A small recess (not shown) at the tip of the stylet is provided wherein tissue is received.

When the stylet slider is fired it will trigger the release of the cannula slider which fires the cannula. The cannula separated the tissue in the recess and the biopsy needle may then be retracted and the tissue sample in the recess removed for analysis.

These subsequent steps following the loading of the biopsy needle are executed as taught in the art and thus do not separately form part of this invention. For example, as mentioned, the arming may be done by applying techniques well-known in the art such as spring loading of both the stylet slide and the cannula slide.

The use of tubes for the two slides is advantageous as they provide an even rotation of the cannula when the cannula and the rotatable head are rotated relative to each other. Although other shapes and elements may be used, these will typically require detailed design and special consideration in order to function correctly.

Moreover, when the cannula tube is formed as a tube, it may function as a guide for the stylet tube.

Figure 14:
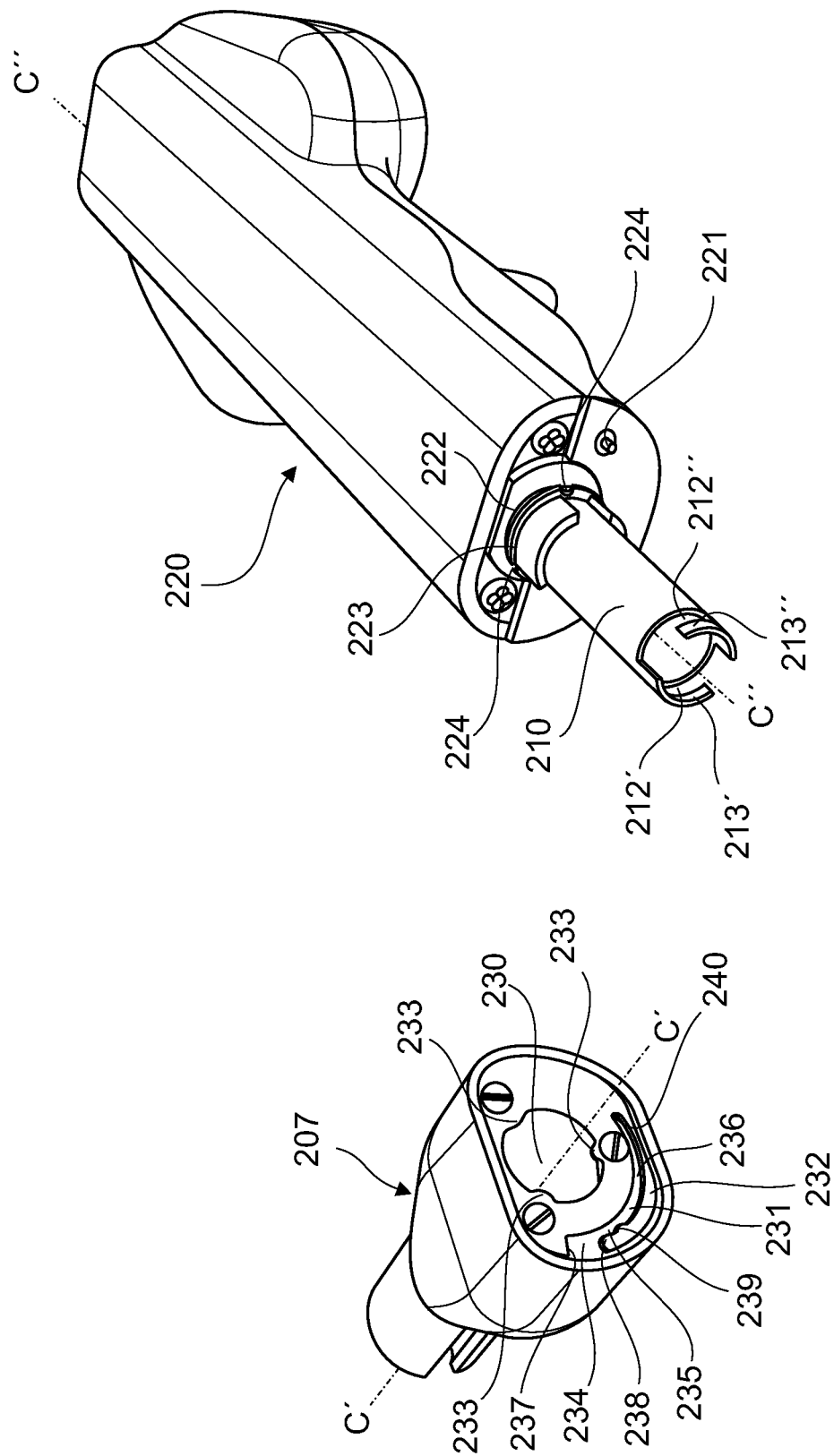
FIGS. 14 and 15 shows the biopsy gun in perspective with the rotatable head detached.
Figure 15:
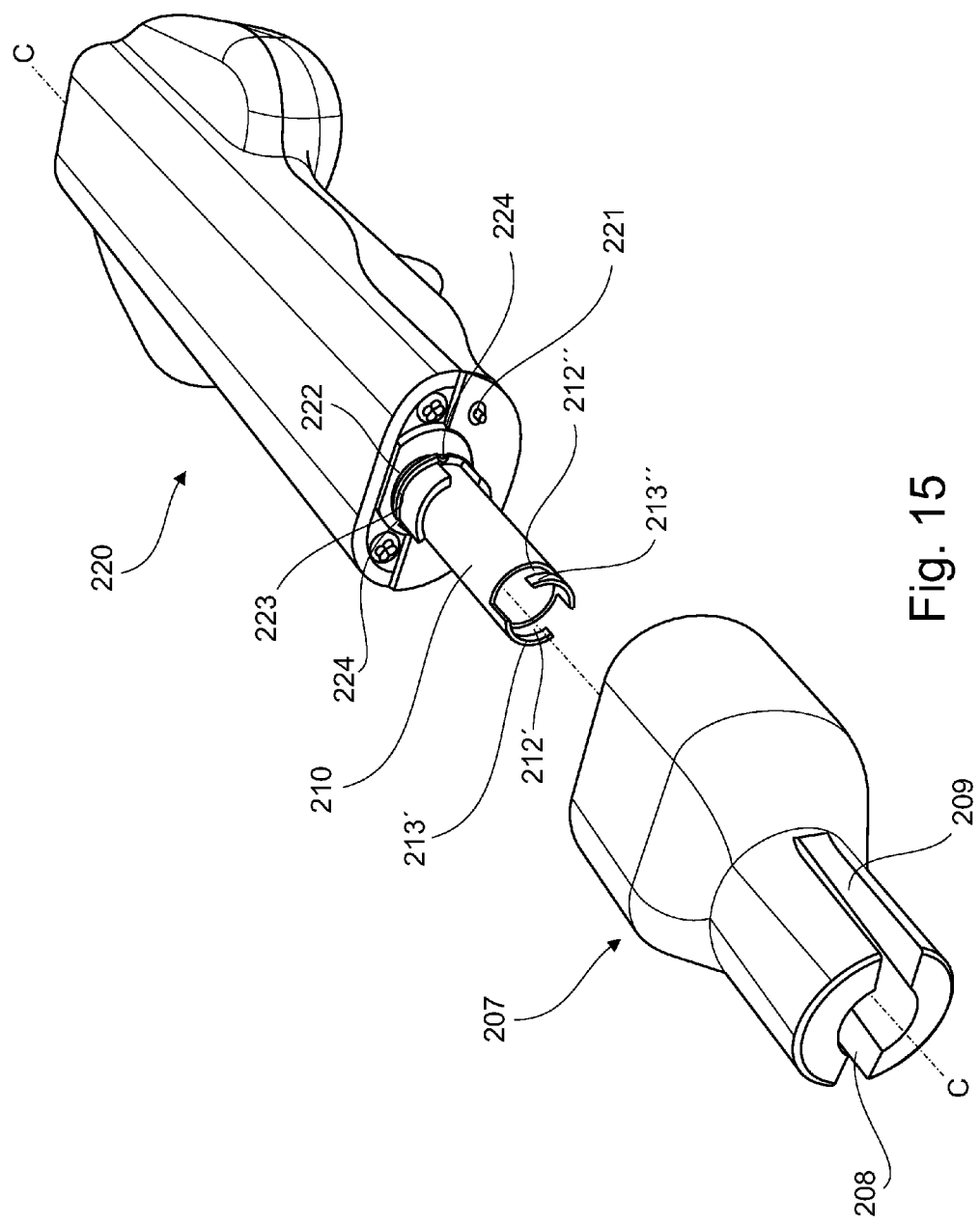

Another advantage of the embodiment of the biopsy gun as described is that the rotatable head 207 of the biopsy gun is detachably arranged on the biopsy gun body 220 as described below with reference to FIGS. 14 and 15.

A through going passage 230 is provided along longitudinal axis C'-C' through the rotatable head 207. The passage 230 is dimensioned to accommodate the part of the cannula tube 210 extending outside the body 220.

A guiding groove 231 is formed in the rotatable head 207 and a guide protrusion 221 extends from the biopsy gun body and has a size that allows it to run in the guiding groove, when the rotatable head is coupled to the biopsy gun. The guiding groove 231 is partly defined by spring arm 232 which may be deflected in a radial direction to the axis C'-C'. The function of the spring arm 232 will be described later.

An annular track 222 extends around the cannula tube 210. The annular track is defined by the biopsy gun body and an annular track rim 223 extending around the cannula tube 210 in a distance from the biopsy gun body. Three track recesses 224 are formed in the track rim 223. Track protrusions 233 are formed on the inside of the through going passage 230.

The track recesses 224 are arranged equiangular around the track rim 223. The track protrusions are formed equiangular around the inside of the through going passage 230. The track recesses are slightly larger than the track protrusion in a way that the protrusions may pass through the recesses and into the track 222 when the axis C'-C' of the rotatable head 207 and the axis C"-C" of the biopsy gun body are co-axially arranged along the axis C-C, as shown in FIG. 15 and the protrusion and the recesses are aligned. The protrusions have a radial extent toward the longitudinal axis C-C which overlaps the radial extent of the track rim 223 away from axis C-C. This allows a locking engagement of the rotatable head and the biopsy gun body when the protrusions are arranged into the track and moved out of alignment with the recesses by rotating the rotatable head and the biopsy gun body relative to each other around axis C-C.

During coupling of the rotatable head and the biopsy gun body the guiding groove 231 and the guide protrusion 221 limits the rotational movement of the head and the body as the protrusion is only allowed to move within the groove. The groove is divided into three sections, a release section 234, a loaded section 235 and a loading section 236. The release section 234 extends between a first end 237 of the groove and a first notch 238 extending radially inwards from the spring arm 232. The loaded section 235 extends between the first notch 238 and a second notch 239, which, like the first notch, also extends radially inwards from the spring arm. The loading section 236 extends between the second notch 239 and a second end 240 of the guiding groove.

Thus, when the biopsy head and body are coupled together, the guide protrusion 221 and the guide groove 231 limits the relative rotation of the part around longitudinal axis C-C. The relative position of the head 207 in respect of the body 220 thereby defines three positions of the biopsy gun; a release position wherein the guide protrusion is in release section 234; a loaded position wherein the guide protrusion is in the loaded section 235; and a loading position wherein the guide protrusion is in the loading section 236.

First and second notches 238,239 are sized in a way that the guiding grooves narrows into a width that is smaller than the width of the guiding protrusion. Thus, when the head and body are rotated relative to each other, the protrusion will come into contact with the respective notches, as it moves between sections. The user then has to use additional forces in order to deflect the spring arm 232 and thereby allowing the protrusion to pass the respective notch. This has the advantage that the user is given a clear indication of when the biopsy gun is in one of the three positions described above. Further, this also prevents that the gun unintentionally moves between positions.

In the release position, the track protrusions 233 and the track recesses 224 are aligned and coupling and decoupling of the rotatable head and biopsy gun body is possible.

In the loading position it is possible to insert a biopsy needle as described herein, in a way that the first and second cannula tabs 150,151 on the biopsy needle may pass the first and second coupling tab 213',213" of the cannula tube 210 in order to be received in the first and second cannula groove 212',212" of the cannula tube 210.

In the loaded position, the rotatable head is rotated, in a way that the first and second coupling tab 213',213" extend across the longitudinal extent of the first and second recesses 208,209 of the rotatable head. In other words, when the biopsy needle as described herein is placed in the biopsy gun and the first and second ribs 137,138 are received in the first and second recesses then the first and second coupling tabs 213',213" engage the first and second cannula tabs 150,151 thereby securing the biopsy needle in the biopsy gun.

Accordingly, when used the biopsy gun is placed in the loading position wherein a biopsy needle is placed in the biopsy gun. Subsequently, the biopsy gun is placed in the loaded position wherein the biopsy gun may be used to retrieve a sample as described above. When a sample has been taken, the biopsy gun is placed back into its loading position whereafter the biopsy needle is removed. In case more samples are needed, then a new needle is inserted and the procedure is repeated.

However, if the procedure is over and the biopsy needle removed, then the biopsy gun is placed in its release position wherein the head is removed. Being able to remove the head is particularly advantageous for cleaning of the instrument. Especially, under some laws it is only required to clean/sterilize the part of the biopsy gun closest to the entry site into the patient, which in this case is the rotatable head. By being able to remove the head, only a small part has to be clean saving time and space.

Figure 10:
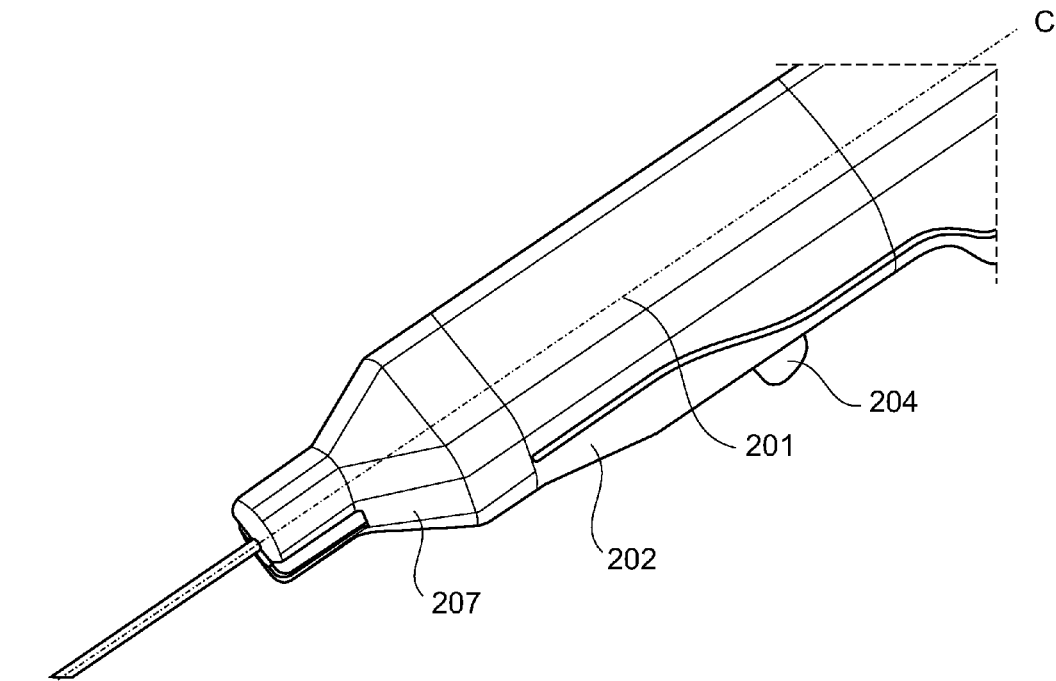
FIG. 10-13 shows the biopsy gun and the biopsy needle in a coupled configuration wherein different parts have been hidden in order to facilitate understanding.

In the described embodiment, the biopsy gun is in the loaded position when the rotatable head is flush with the biopsy gun body such as shown in FIG. 10. When the head is turned counter clockwise 90° relative to the body form, the loaded position is then placed in the loading position and when the head is turned clockwise 45° relative to the body from the loaded position, then it is placed in the release position.

The invention claimed is:

1. A method of loading a locked tissue biopsy needle into a biopsy gun that is provided along with the locked tissue biopsy needle, the method comprising:
   rotating a head of the biopsy gun in a first direction, with the head located at a front distal portion of the biopsy gun;
   inserting the locked tissue biopsy needle into a distal end of the head of the biopsy gun, with the locked tissue biopsy needle providing a stylet inserted in a longitudinal lumen of a cannula, and the stylet locked in position relative to the cannula thus preventing longitudinal movement of the stylet within the cannula; and
   rotating the head of the biopsy gun in a second direction opposite from the first direction and rotating the stylet relative to the cannula and unlocking the stylet from the cannula allowing longitudinal movement of the stylet within the cannula.

2. The method of claim 1, comprising providing the cannula with a track including a longitudinal slot communicating with a lateral slot and providing the stylet with a radial protrusion sized to be received in the track of the cannula; and
   engaging the radial protrusion of the stylet in the lateral slot of the track of the cannula and locking the stylet relative to the cannula.

3. The method of claim 2, comprising engaging the radial protrusion of the stylet in the longitudinal slot of the track of the cannula and unlocking the stylet relative to the cannula allowing longitudinal movement of the stylet within the cannula by allowing longitudinal movement of the radial protrusion of the stylet within the longitudinal slot of the track of the cannula.

4. The method of claim 2, comprising rotating the head of the biopsy gun in the second direction and rotating the cannula in the second direction and disengaging the radial protrusion of the stylet from the lateral slot of the track of the cannula.

5. The method of claim 2, comprising rotating the head of the biopsy gun in the second direction and rotating the cannula in the second direction and engaging the radial protrusion of the stylet with the longitudinal slot of the track of the cannula.

6. The method of claim 1, comprising providing the cannula with a cannula rib fixed to and extending in a radial direction away from the lumen of the cannula and inserting the cannula rib of the locked tissue biopsy needle into a recess formed in the distal end of the head of the biopsy gun.

7. The method of claim 6, comprising rotating the head of the biopsy gun in the second direction and rotating the cannula rib in the second direction and rotating the cannula relative to the stylet and unlocking the stylet from the cannula.

8. A method of loading a biopsy needle into a biopsy gun that is provided with the biopsy needle, the method comprising:
   providing the biopsy needle with a stylet inserted in a longitudinal lumen of a cannula;
   providing the cannula with a track including a longitudinal slot communicating with a lateral slot;
   providing the stylet with a radial protrusion sized to be received in the track of the cannula;
   configuring the biopsy needle to be lockable by locking the stylet relative to the cannula by engaging the radial protrusion of the stylet within the lateral slot of the cannula and thus preventing longitudinal movement of the stylet within the longitudinal lumen of the cannula;
   inserting the biopsy needle into a front distal end of a head of the biopsy gun;
   rotating the head of the biopsy gun in a first direction and rotating the cannula relative to the stylet and disengaging the radial protrusion of the stylet from the lateral slot of the track of the cannula thus unlocking the stylet from the cannula and allowing longitudinal movement of the stylet within the longitudinal lumen of the cannula.

9. The method of claim 8, comprising providing the cannula with a cannula rib fixed to and extending in a radial direction away from the lumen of the cannula and inserting the cannula rib of the into a recess formed in the front distal end of the head of the biopsy gun.

10. The method of claim 9, wherein rotating the cannula relative to the stylet comprises rotating the head of the biopsy gun and rotating the cannula rib of the cannula relative to the stylet.

* * * * *